(12) United States Patent
Keenan et al.

(10) Patent No.: US 10,117,980 B2
(45) Date of Patent: Nov. 6, 2018

(54) DISTAL BEARING SUPPORT

(71) Applicant: TC1 LLC, Pleasanton, CA (US)

(72) Inventors: Richard L. Keenan, Livermore, CA (US); Keif M. Fitzgerald, San Jose, CA (US)

(73) Assignee: TC1 LLC, Pleasanton, CA (US)

( * ) Notice: Subject to any disclaimer, the term of this patent is extended or adjusted under 35 U.S.C. 154(b) by 0 days.

(21) Appl. No.: 15/266,864

(22) Filed: Sep. 15, 2016

(65) Prior Publication Data

US 2017/0087287 A1 Mar. 30, 2017

Related U.S. Application Data

(63) Continuation of application No. 13/802,556, filed on Mar. 13, 2013, now Pat. No. 9,446,179.
(Continued)

(51) Int. Cl.
*A61M 5/00* (2006.01)
*A61M 1/10* (2006.01)
(Continued)

(52) U.S. Cl.
CPC ............ *A61M 1/10* (2013.01); *A61M 1/1013* (2014.02); *A61M 1/1024* (2014.02);
(Continued)

(58) Field of Classification Search
CPC .. A61M 1/101; A61M 1/1024; A61M 1/1013; A61M 1/122; A61M 1/10;
(Continued)

(56) References Cited

U.S. PATENT DOCUMENTS

| | | |
|---|---|---|
| 1,902,418 A | 3/1933 | Pilgrim |
| 2,356,659 A | 10/1942 | Aguiar |

(Continued)

FOREIGN PATENT DOCUMENTS

| | | |
|---|---|---|
| CA | 2256427 A1 | 10/1998 |
| CA | 2322012 | 8/2000 |

(Continued)

OTHER PUBLICATIONS

Abiomed, "Impella 5.0 with the Impella Console, Circulatory Support System, Instructions for Use & Clinical Reference Manual," Jun. 2010, in 122 pages.
(Continued)

*Primary Examiner* — Ariana Zimbouski
(74) *Attorney, Agent, or Firm* — Armstrong Teasdale LLP

(57) ABSTRACT

In various embodiments, a catheter pump is disclosed herein. The catheter pump can include an elongated catheter body having a distal portion including an expandable cannula having an inlet and an outlet. The expandable cannula can have a delivery profile and an operational profile larger than the delivery profile. An impeller assembly can include an impeller shaft, and an impeller body can include one or more blades. The impeller blades can draw blood into the cannula when rotated. Further, an expandable support can have a mounting portion disposed on the impeller shaft distal of the impeller body and a cannula contact portion for reducing a change in tip gap due to bending of the cannula. The cannula contact portion can be disposed distal of the mounting portion.

21 Claims, 10 Drawing Sheets

Related U.S. Application Data

(60) Provisional application No. 61/646,755, filed on May 14, 2012.

(51) Int. Cl.
  *A61M 1/12* (2006.01)
  *F04D 1/00* (2006.01)
  *F04D 25/06* (2006.01)

(52) U.S. Cl.
  CPC ............ *A61M 1/122* (2014.02); *A61M 1/101* (2013.01); *A61M 1/1017* (2014.02); *A61M 1/1034* (2014.02); *A61M 1/125* (2014.02); *F04D 1/00* (2013.01); *F04D 25/06* (2013.01)

(58) Field of Classification Search
  CPC .. A61M 1/1074; A61M 1/1072; A61M 1/107; A61M 1/125; A61M 1/1017; A61M 1/1034; F04D 13/00; F04D 13/02; F04D 19/00; F04D 1/00; F04D 25/06
  See application file for complete search history.

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Voider |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,045,072 A | 9/1991 | Castillo et al. |
| 5,049,134 A | 9/1991 | Golding et al. |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub et al. |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens |
| 5,868,703 A | 2/1999 | Bertolero |
| 5,888,241 A | 3/1999 | Jarvik |
| 5,888,242 A | 3/1999 | Antaki et al. |

(56) References Cited

U.S. PATENT DOCUMENTS

| | | |
|---|---|---|
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A * | 10/1999 | Siess ............... A61M 1/101 415/900 |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III et al. |
| 6,053,705 A | 4/2000 | Schob et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 * | 10/2002 | Pelton ...................... A61F 2/95 606/194 |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Grundeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,860,713 B2 | 3/2005 | Hoover |
| 6,866,625 B1 | 3/2005 | Avre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez |
| 7,605,298 B2 | 10/2009 | Bechert et al. |
| 7,619,560 B2 | 11/2009 | Penna |
| 7,633,193 B2 | 12/2009 | Masoudipour et al. |
| 7,645,225 B2 | 1/2010 | Medvedev et al. |

(56) References Cited

U.S. PATENT DOCUMENTS

| | | |
|---|---|---|
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 * | 4/2014 | Nunez ................. A61M 1/125 600/16 |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | LaRose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2002/0107506 A1 | 8/2002 | McGuckin, Jr. et al. |
| 2002/0111663 A1 | 8/2002 | Dahl et al. |
| 2002/0151761 A1 | 10/2002 | Viole et al. |
| 2002/0169413 A1 | 11/2002 | Keren et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0019251 A1 | 1/2004 | Viole et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0236173 A1 | 11/2004 | Viole et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165269 A9 | 7/2005 | Aboul-Hosn et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0018943 A1 | 1/2006 | Bechert et al. |
| 2006/0036127 A1 | 2/2006 | Delgado |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0156006 A1 | 7/2007 | Smith et al. |
| 2007/0203442 A1 | 8/2007 | Bechert et al. |
| 2007/0208298 A1 | 9/2007 | Ainsworth et al. |
| 2007/0233270 A1 | 10/2007 | Weber et al. |
| 2007/0282417 A1 | 12/2007 | Houston et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflete |
| 2008/0167679 A1 | 7/2008 | Papp |
| 2008/0275290 A1 | 11/2008 | Viole et al. |
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0060743 A1 | 3/2009 | McBride et al. |
| 2009/0062597 A1 | 3/2009 | Shifflette |
| 2009/0073037 A1 | 3/2009 | Penna |

(56) References Cited

U.S. PATENT DOCUMENTS

| | | |
|---|---|---|
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | LaRose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0016960 A1 | 1/2010 | Bolling |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0127871 A1 | 5/2010 | Pontin |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1* | 1/2011 | Campbell ............ A61M 1/1072 600/16 |
| 2011/0004291 A1 | 1/2011 | Davis et al. |
| 2011/0021865 A1 | 1/2011 | Aboul-Hosn et al. |
| 2011/0034874 A1 | 2/2011 | Reitan |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0236210 A1 | 9/2011 | McBride et al. |
| 2011/0237863 A1 | 9/2011 | Ricci et al. |
| 2011/0257462 A1 | 10/2011 | Rodefeld |
| 2011/0270182 A1 | 11/2011 | Breznock et al. |
| 2011/0275884 A1 | 11/2011 | Scheckel |
| 2012/0004495 A1 | 1/2012 | Bolling |
| 2012/0029265 A1 | 2/2012 | LaRose et al. |
| 2012/0059213 A1 | 3/2012 | Spence |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0237357 A1 | 9/2012 | Schumacher et al. |
| 2012/0245404 A1 | 9/2012 | Smith et al. |
| 2012/0265002 A1 | 10/2012 | Roehn et al. |
| 2013/0041202 A1 | 2/2013 | Toellner |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher |
| 2013/0303831 A1 | 11/2013 | Evans |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0067057 A1 | 3/2014 | Callaway et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng et al. |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | LaRose et al. |
| 2015/0051435 A1 | 2/2015 | Siess et al. |
| 2015/0051436 A1 | 2/2015 | Spanier et al. |
| 2015/0080743 A1 | 3/2015 | Siess |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov |
| 2015/0209498 A1 | 7/2015 | Franono et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher et al. |
| 2016/0256620 A1 | 9/2016 | Scheckel et al. |

FOREIGN PATENT DOCUMENTS

| | | |
|---|---|---|
| CA | 2367469 | 10/2000 |
| CA | 2407938 | 11/2002 |
| CA | 2480467 | 8/2003 |
| CA | 2701810 | 4/2009 |
| DE | 196 13 565 | 10/1997 |
| EP | 0 364 293 | 4/1990 |
| EP | 0 453 234 | 10/1991 |
| EP | 0 533 432 | 9/1992 |
| EP | 1 207 934 | 5/2002 |
| EP | 1 393 762 A1 | 3/2004 |
| EP | 1 591 079 A1 | 11/2005 |
| EP | 2 151 257 | 2/2010 |
| EP | 2 263 732 | 12/2010 |
| EP | 2 298 374 A1 | 3/2011 |
| FR | 2267800 | 4/1974 |
| GB | 2 239 675 A | 7/1991 |
| JP | S48-23295 | 3/1973 |
| JP | S58-190448 | 7/1983 |
| JP | 06-114101 | 4/1994 |
| JP | H08-500512 | 1/1996 |
| JP | H08-501466 | 2/1996 |
| JP | 10-099447 | 4/1998 |
| JP | 2002-505168 | 2/2002 |
| JP | 2004-514506 | 5/2004 |
| JP | 2011-157961 | 8/2011 |
| TW | 500877 | 9/2002 |
| WO | WO 89/04644 | 6/1989 |
| WO | WO 89/05164 | 6/1989 |
| WO | WO 94/05347 | 3/1994 |
| WO | WO 94/06486 | 3/1994 |
| WO | WO 95/26695 | 10/1995 |
| WO | WO 97/15228 | 5/1997 |
| WO | WO 97/37697 | 10/1997 |
| WO | WO 99/00368 | 1/1999 |
| WO | WO 99/02204 | 1/1999 |
| WO | WO 99/16387 | 4/1999 |
| WO | WO 99/37352 | 7/1999 |
| WO | WO 99/44651 | 9/1999 |
| WO | WO 99/44670 | 9/1999 |
| WO | WO 99/59652 | 11/1999 |
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 00/37139 | 6/2000 |
| WO | WO 00/38591 | 7/2000 |
| WO | WO 00/41612 | 7/2000 |
| WO | WO 00/043053 | 7/2000 |

(56) References Cited

FOREIGN PATENT DOCUMENTS

| WO | WO 00/43062 | 7/2000 |
|---|---|---|
| WO | WO 00/45874 | 8/2000 |
| WO | WO 00/61207 | 10/2000 |
| WO | WO 00/69489 | 11/2000 |
| WO | WO 01/17581 A2 | 3/2001 |
| WO | WO 01/24867 | 4/2001 |
| WO | WO 01/78807 | 10/2001 |
| WO | WO 01/83016 | 11/2001 |
| WO | WO 02/043791 | 6/2002 |
| WO | WO 02/070039 | 9/2002 |
| WO | WO 03/048582 | 6/2003 |
| WO | WO 03/068303 | 8/2003 |
| WO | WO 03/070299 | 8/2003 |
| WO | WO 03/103745 | 12/2003 |
| WO | WO 2005/089674 | 9/2005 |
| WO | WO 2005/123158 | 12/2005 |
| WO | WO 2006/034158 | 3/2006 |
| WO | WO 2006/046779 | 5/2006 |
| WO | WO 2006/051023 | 5/2006 |
| WO | WO 2007/112033 | 10/2007 |
| WO | WO 2008/034068 | 3/2008 |
| WO | WO 2009/073037 | 6/2009 |
| WO | WO 2009/076460 A2 | 6/2009 |
| WO | WO 2010/063494 A1 | 6/2010 |
| WO | WO 2010/127871 | 11/2010 |
| WO | WO 2010/133567 | 11/2010 |
| WO | WO 2010/149393 | 12/2010 |
| WO | WO 2011/003043 | 1/2011 |
| WO | WO 2011/035926 | 3/2011 |
| WO | WO 2011/035927 | 3/2011 |
| WO | WO 2011/035929 | 3/2011 |
| WO | WO 2011/039091 A1 | 4/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |
| WO | WO 2012/094525 | 7/2012 |
| WO | WO 2012/094534 | 7/2012 |
| WO | WO 2013/148697 A1 | 10/2013 |
| WO | WO 2013/160407 A1 | 10/2013 |
| WO | WO 2013/173245 | 11/2013 |
| WO | WO 2014/019274 A1 | 2/2014 |
| WO | WO 2015/063277 | 5/2015 |

OTHER PUBLICATIONS

Abiomed—Recovering Hearts. Saving Lives., Impella 2.5 System, Instructions for Use, Jul. 2007, in 86 sheets.
Aboul-Hosn et al., "The Hemopump: Clinical Results and Future Applications", Assisted Circulation 4, 1995, in 14 pages.
Barras et al., "Nitinol—Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended European Search Report received in European Patent Application No. 07753903.9, dated Oct. 8, 2012, in 7 pages.
Extended European Search Report received in European Patent Application No. 13790890.1, dated Jan. 7, 2016, in 6 pages.
Extended European Search Report received in European Patent Application No. 13791118.6, dated Jan. 7, 2016, in 6 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 6 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04853, dated Jul. 26, 2004, in 5 pages.
International Preliminary Examination Report received in International Patent Application No. PCT/US2003/04401, dated May 18, 2004, in 4 pages.
International Preliminary Report on Patentability and Written Opinion of the International Searching Authority received in International Patent Application No. PCT/US2005/033416, dated Mar. 20, 2007, in 7 pages.
International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020553, dated Aug. 17, 2012, in 8 pages.
International Search Report and Written Opinion received in International Patent Application No. PCT/US2012/020383, dated Aug. 17, 2012; in 9 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.

(56) References Cited

OTHER PUBLICATIONS

International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 17 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020878, dated May 7, 2014, in 13 pages.
International Search Reort and Written Opinion received in International Patent Application No. PCT/US2015/026013, dated Jul. 8, 2015, in 12 pages.
International Search Report and Written Opinion received in International Patent Application No. PCT/US2015/026014, dated Jul. 15, 2015, in 13 pages.
International Search Report and Written Opinion received in International Patent Application No. PCT/US2015/026025, dated Jul. 20, 2015, in 12 pages.
International Search Report and Written Opinion received in International Patent Application No. PCT/US2015/025959, dated Aug. 28, 2015, in 16 pages.
International Search Report and Written Opinion received in International Patent Application No. PCT/US2015/025960, dated Sep. 3, 2015, in 15 pages.
International Search Report and Written Opinion received in International Patent Application No. PCT/US2015/045370, dated Nov. 18, 2015, in 12 pages.
International Search Report and Written Opinion received in International Patent Application No. PCT/US2016/014371, dated May 2, 2016, in 18 pages.
International Search Report and Written Opinion received in International Patent Application No. PCT/US2016/014391, dated May 2, 2016, in 17 pages.
International Search Report received in International Patent Application No. PCT/US2003/004401, dated Nov. 10, 2003, in 9 pages.
International Search Report received in International Patent Application No. PCT/US2003/004853, dated Jul. 3, 2003, in 3 pages.
International Search Report Written Opinion received in International Patent Application No. PCT/US2010/040847, dated Dec. 14, 2010, in 17 pages.
JOMED Reitan Catheter Pump RCP, Percutaneous Circulatory Support, in 10 pages, believed to be published prior to Oct. 15, 2003.
JOMED Reitan Catheter Pump RCP, Feb. 18, 2003, in 4 pages.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).

Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Sieß et al., "Hydraulic refinement of an intraarterial microaxial blood pump", The International Journal of Artificial Organs, 1995, vol. 18, No. 5, pp. 273-285.
Sieß, "Systemanalyse and Entwicklung intravasaler Rotationspumpen zur Herzunterstützung", Helmholtz-Institut fur Blomedixinische Technik an der RWTH Aachen, Jun. 24, 1998, in 105 pages.
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.

(56) References Cited

OTHER PUBLICATIONS

Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, a Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, a Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
Extended European Search Report received in European Patent Application No. 14779928.2, dated Oct. 7, 2016, in 6 pages.
International Search Report and Written Opinion received in International Patent Application No. PCT/US2016/014379, dated Jul. 25, 2016, in 19 pages.
Extended European Search Report received in European Patent Application No. 14764392.8, dated Oct. 27, 2016, in 7 pages.
Schmitz-Rode et al., "Axial flow catheter pump for circulatory support," Biomedizinische Technik, 2002, Band 47, Erganzungsband 1, Teil 1, pp. 142-143.

* cited by examiner

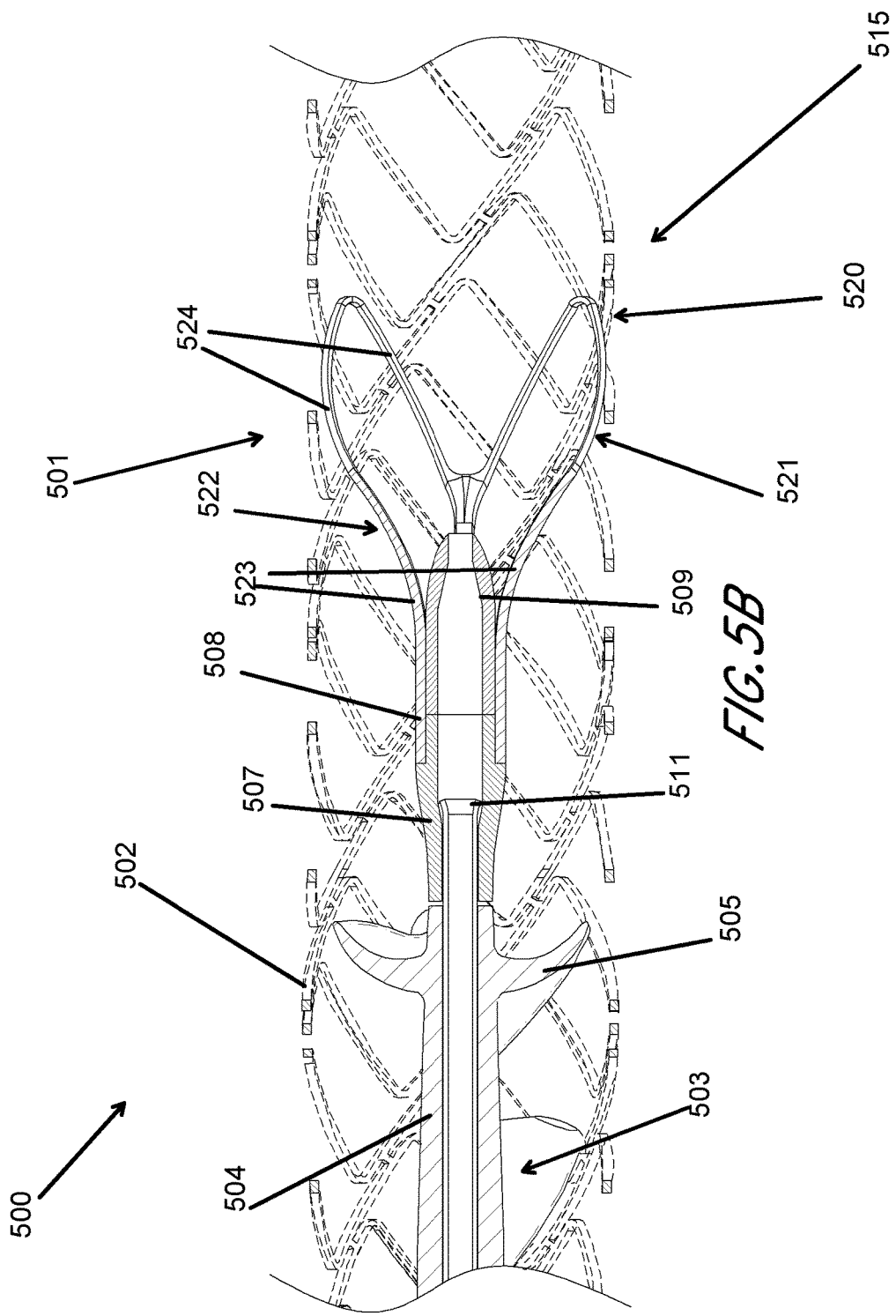

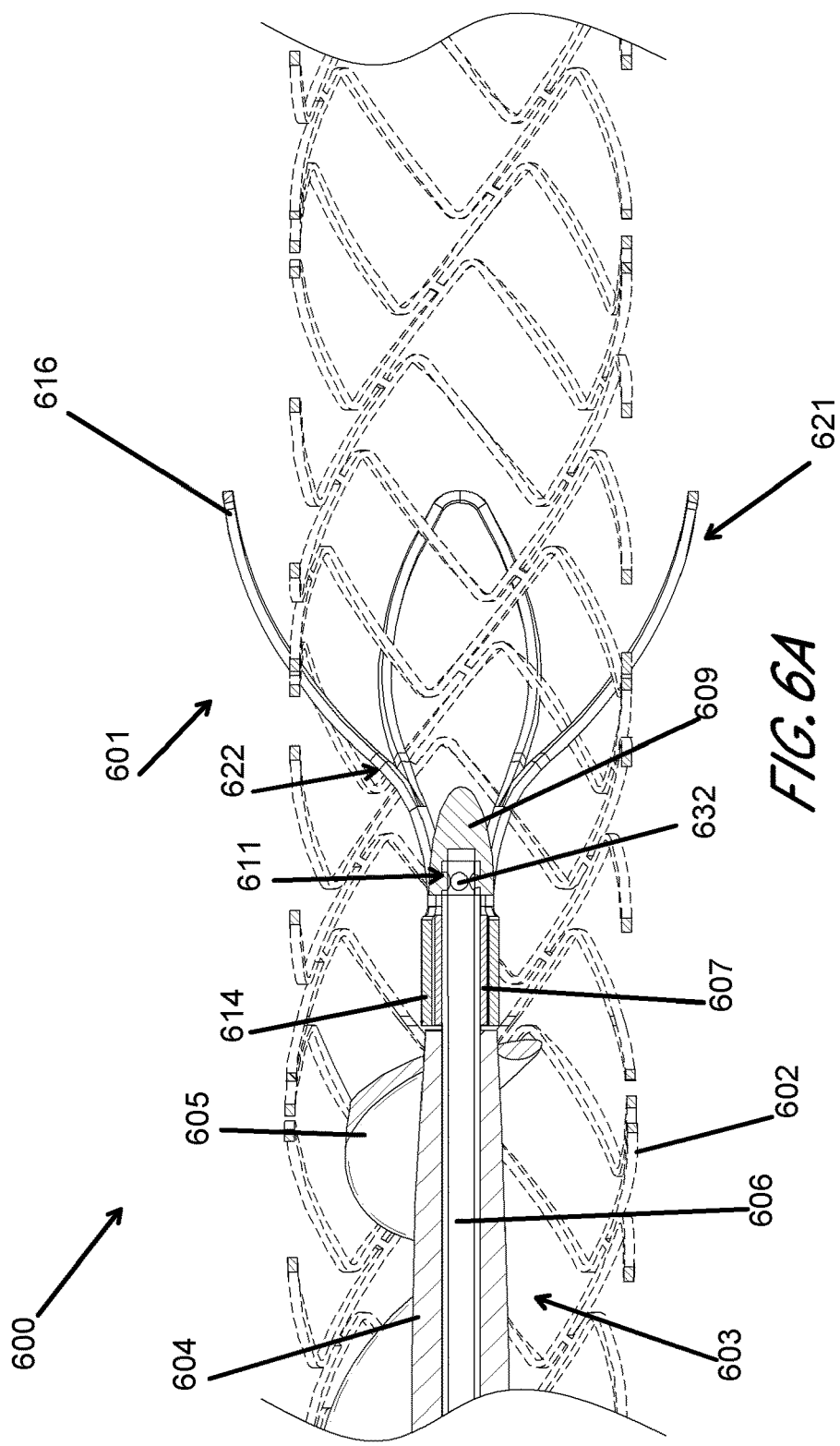

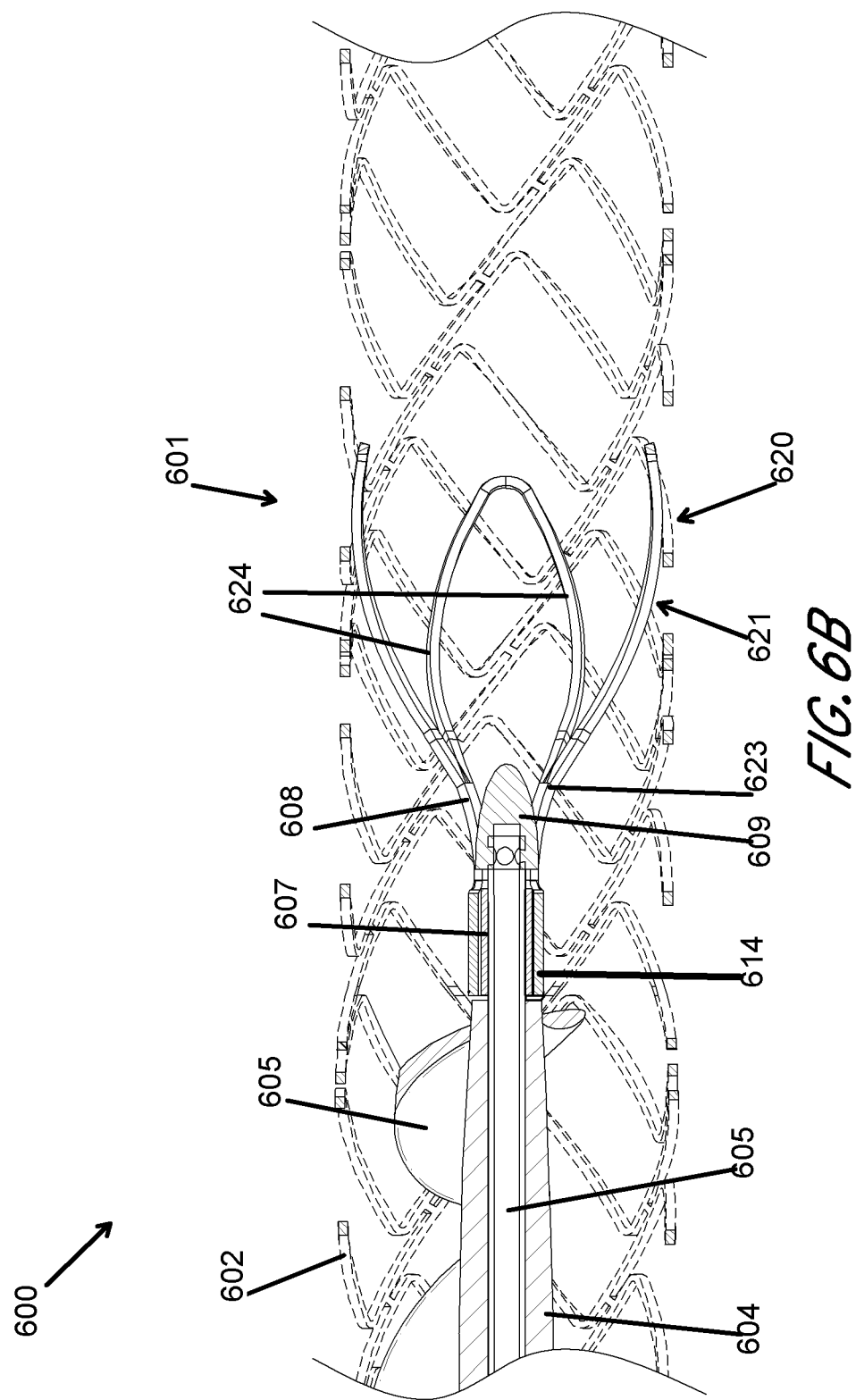

DISTAL BEARING SUPPORT

INCORPORATION BY REFERENCE TO ANY PRIORITY APPLICATIONS

Any and all applications for which a foreign or domestic priority claim is identified in the Application Data Sheet as filed with the present application, including U.S. application Ser. No. 13/802,556, filed Mar. 13, 2013, and U.S. Application No. 61/646,755, filed May 14, 2012, both entitled Distal Bearing Support, are hereby incorporated by reference under 37 CFR § 1.57 in their entirety and for all purposes.

BACKGROUND OF THE INVENTION

Field of the Invention

This application is directed to pumps for mechanical circulatory support of a heart. In particular, this application is directed to support structures for an impeller assembly that can be used in a catheter pump.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow while minimizing the likelihood of hemolysis at high rotational speeds. These and other problems are overcome by the inventions described herein.

Further, there is a need for providing an operative device of the pump capable of pumping blood at high flow rates while reducing the risk of hemolysis at the operative device. For example, when an impeller assembly is provided at the operative device, the high rate of rotation of the impeller may cause hemolysis, as blood flows past the high-speed impeller. Accordingly, there is a need for reducing the risk of hemolysis at the operative device of the pump, particularly when movable components are disposed at the operative device.

SUMMARY OF THE INVENTION

There is an urgent need for a pumping device that can be inserted percutaneously and also provide full cardiac rate flows of the left, right, or both the left and right sides of the heart when called for.

In one embodiment, a catheter pump is disclosed. The catheter pump can include an elongated catheter body having a distal portion including an expandable cannula having an inlet and an outlet. The expandable cannula can have a delivery profile and an operational profile larger than the delivery profile. An impeller assembly can include an impeller shaft, and an impeller body can include one or more blades. The impeller blades can draw blood into the cannula when rotated. Further, an expandable support can have a mounting portion disposed on the impeller shaft distal of the impeller body and configured to maintain a position of the impeller relative to a cannula wall. In some embodiments, a motor can be disposed at a proximal end of the elongate catheter body, such that the motor remains remote from the impeller outside the patient in use. A re-sealable member can be disposed distally of the impeller in some embodiments. Further, the re-sealable member can be coupled with a bearing coupled with the impeller enabling the impeller to rotate in the bearing structure while holding the re-sealable member stationary distal of but aligned with the impeller.

In another embodiment, a catheter pump is disclosed. The catheter pump can comprise an elongated catheter body having a distal portion including an expandable cannula having an inlet and an outlet. The expandable cannula can have a delivery profile and an operational profile larger than the delivery profile. An impeller can include a tubular body and at least one blade disposed about the tubular body for drawing blood into the cannula when the impeller is rotated. A re-sealable member can be disposed distally of the tubular body in a guidewire passage. The re-sealable member can be coupled with the tubular body in a manner permitting the tubular body to rotate while the re-sealable member is not rotated.

In yet another embodiment, an apparatus for inducing motion of a fluid relative to the apparatus is disclosed. The apparatus can comprise a motor. An elongated catheter body can be coupled with the motor. The catheter body can include an expandable distal portion having an inlet and an outlet and a support structure disposed about a lumen. The expandable distal portion can have a delivery profile and an operational profile larger than the delivery profile. The apparatus can include an impeller comprising at least one impeller blade. The apparatus can further include an expandable impeller support having an arcuate outer surface in contact with the support structure at least when the expandable distal portion has the operational profile. Operation of the motor can cause rotation of the impeller to draw blood into the lumen. In some embodiments, the motor can be disposed at a proximal end of the elongate catheter body, such that the motor remains remote from the impeller outside the patient in use. A re-sealable member can be disposed distally of the impeller in some embodiments. Further, the re-sealable member can be coupled with a bearing coupled with the impeller enabling the impeller to rotate in the bearing structure while holding the re-sealable member stationary distal of but aligned with the impeller.

BRIEF DESCRIPTION OF THE DRAWINGS

A more complete appreciation of the subject matter of this application and the various advantages thereof can be realized by reference to the following detailed description, in which reference is made to the accompanying drawings in which:

FIGS. 5A-5B show cross-sectional views of one embodiment of a distal bearing support;

FIGS. 6A and 6B show cross-sectional views of another embodiment of a distal bearing support.

Figure 1:
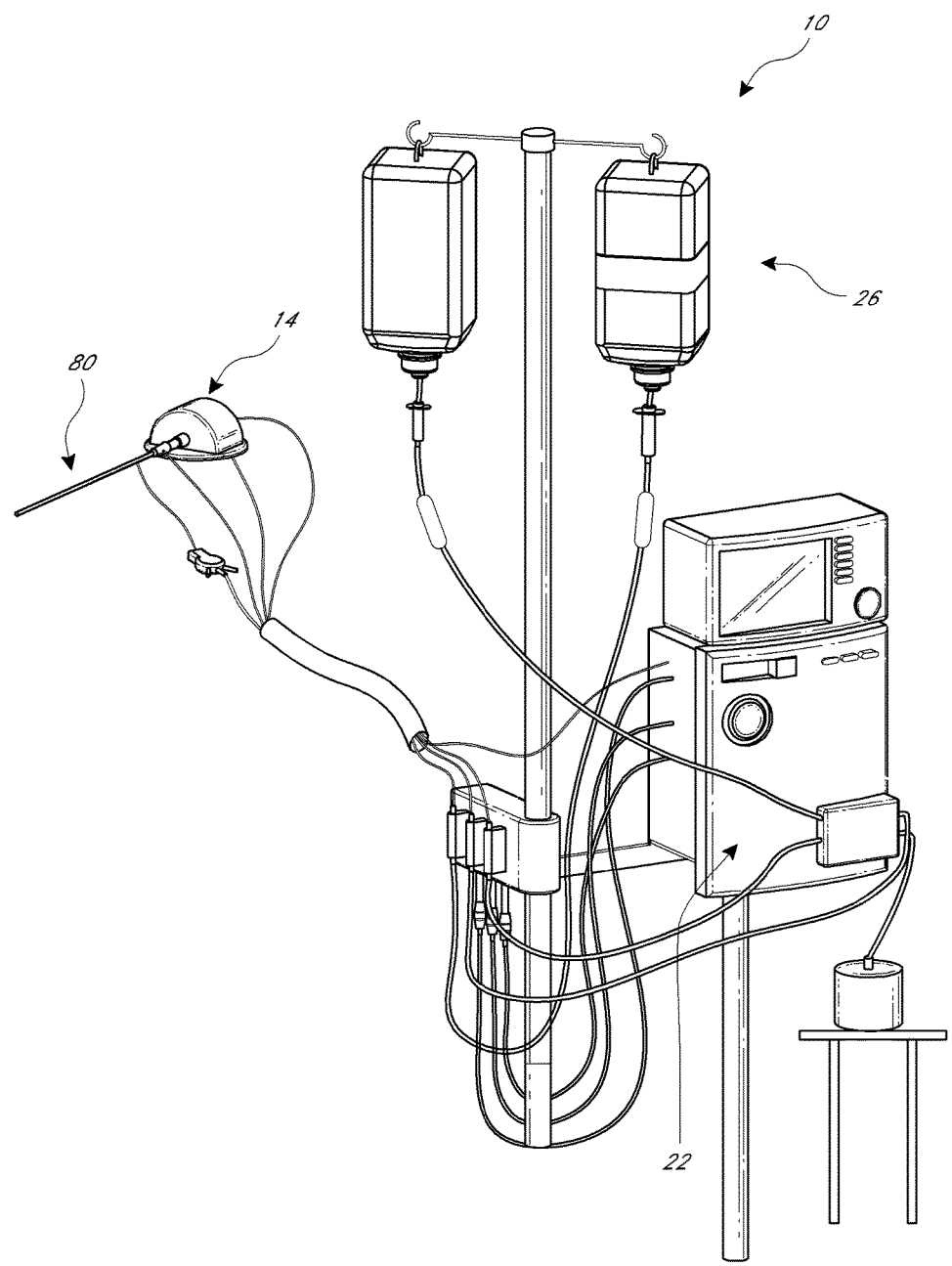
FIG. 1 illustrates one embodiment of a catheter pump configured for percutaneous application and operation.

More detailed descriptions of various embodiments of components for heart pumps useful to treat patients experiencing cardiac stress, including acute heart failure, are set forth below.

DETAILED DESCRIPTION OF THE PREFERRED EMBODIMENT

This application is directed to apparatuses for inducing motion of a fluid relative to the apparatus. In particular, the disclosed embodiments generally relate to various configurations for supporting an impeller disposed at a distal portion of a percutaneous catheter pump. As discussed in greater detail below, such supporting structure can be advantageous to minimize excursion of a high speed impeller toward or into a structure forming an inside surface of a cannula within which the impeller rotates. For example, in the disclosed embodiments, the cannula can be flexible, and the impeller can be flexibly supported off a distal end of the impeller shaft by a support member. In addition, the disclosed supporting structure can be advantageous at high impeller speeds and when the impeller and cannula are subject to hydraulic forces. The disclosed supports can act in various embodiments to maintain separation between the cannula and the impeller under various conditions. This support structure is particularly challenging for embodiments in which one or both of the impeller and cannula are collapsed or compressed for insertion of the pump. Furthermore, a re-sealable tip can be disposed near the distal end of the impeller. The re-sealable member can be configured to seal a guidewire guide tube when the guidewire guide tube and/or a guidewire are withdrawn from the pump.

I. Catheter Pump System and Method

FIGS. 1-4 show aspects of one embodiment of a catheter pump 10 that can provide high performance flow rates. Various additional aspects of the pump and associated components are similar to those disclosed in U.S. Pat. Nos. 7,393,181, 8,376,707, 7,841,976, 7,022,100, and 7,998,054 and U.S. Pub. Nos. 2011/0004046, 2012/0178986, 2012/0172655, 2012/0178985, and 2012/0004495, the entire contents of which are incorporated herein for all purposes by reference. In addition, this application incorporates by reference in its entirety and for all purposes the subject matter disclosed in each of the following concurrently filed applications: Application No. 61/780,656, entitled "FLUID HANDLING SYSTEM," filed on the same date as this application; U.S. application Ser. No. 13/801,833, entitled "SHEATH SYSTEM FOR CATHETER PUMP," filed on the same date as this application; U.S. application Ser. No. 13/802,570, entitled "IMPELLER FOR CATHETER PUMP," filed on the same date as this application; U.S. application Ser. No. 13/801,528, entitled "CATHETER PUMP," filed on the same date as this application; and U.S. application Ser. No. 13/802,468, entitled "MOTOR ASSEMBLY FOR CATHETER PUMP," filed on the same date as this application.

A. Catheter Pump System

The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. No. 5,964,694; U.S. Pat. No. 6,007,478; U.S. Pat. No. 6,178,922; and U.S. Pat. No. 6,176,848, all of which are hereby incorporated by reference herein in their entirety for all purposes.

Figure 2:
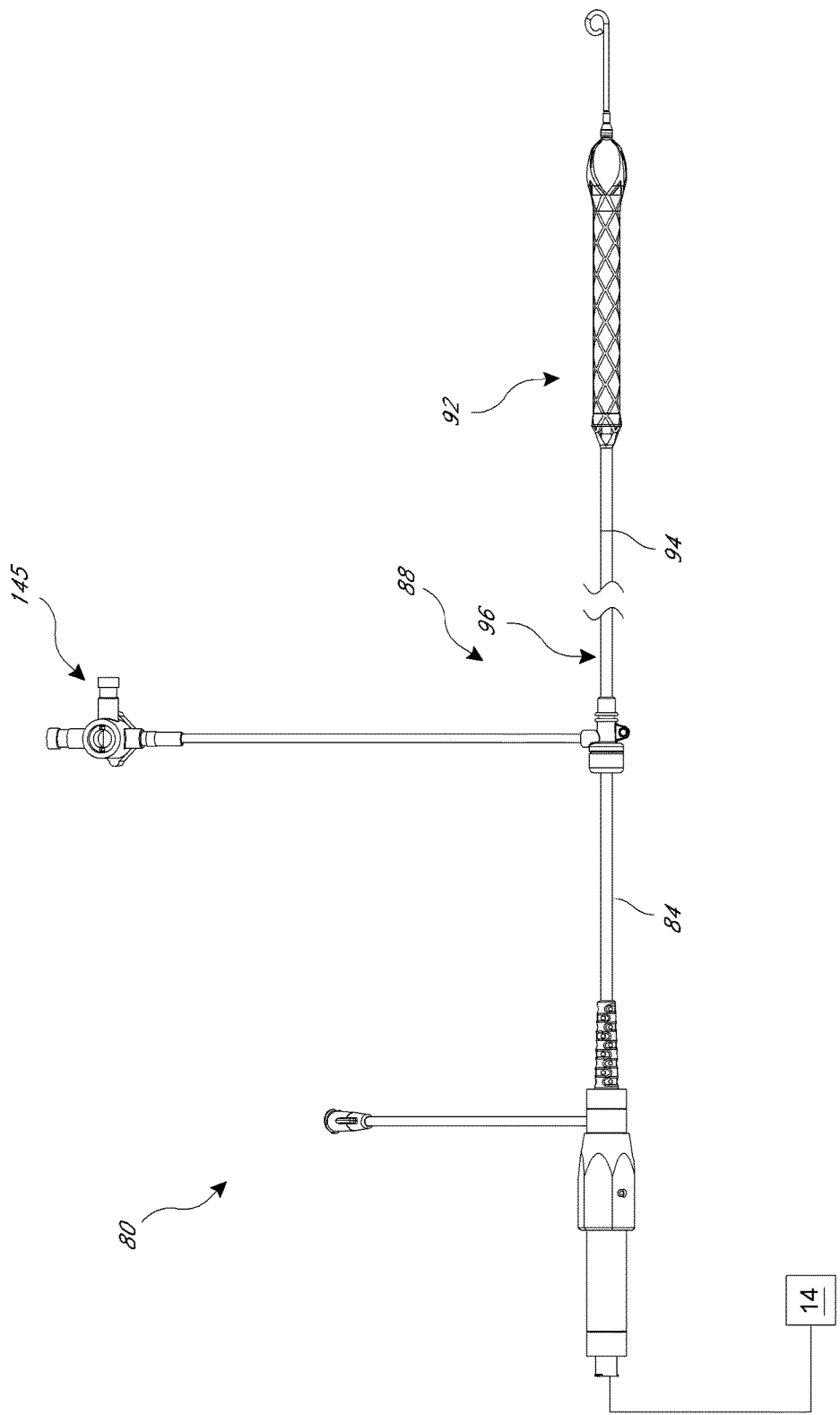
FIG. 2 is a plan view of one embodiment of a catheter assembly adapted to be used with the catheter pump of FIG. 1.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88. One embodiment of a blood flow assembly 92 is coupled with the distal end of the catheter body 84. At least a portion of the blood flow assembly 92 is expandable and collapsible. For example, the blood flow assembly 92 can include an expandable and collapsible cannula. The cannula can be formed of a superelastic material, and in some embodiments, may have various shape memory material properties. The blood flow assembly 92 also can include an expandable and collapsible impeller. The cannula and impeller are discussed more below. In the collapsed state, the distal end of the catheter system 80 can be advanced to the heart, for example, through an artery. In the expanded state the blood flow assembly 92 is able to pump or output blood at high flow rates. FIGS. 2-4 illustrate the expanded state of one embodiment. The collapsed state can be provided by advancing a distal end 94 of an elongate body 96 of the sheath assembly 88 distally over the cannula of the blood flow assembly 92 to cause the blood flow assembly 92 to collapse. This provides an outer profile throughout the catheter assembly 80 that is of small diameter, for example a catheter size of about 12.5 Fr.

B. Impeller and Cannula Features, Deployment, and Operation

Figure 3A:
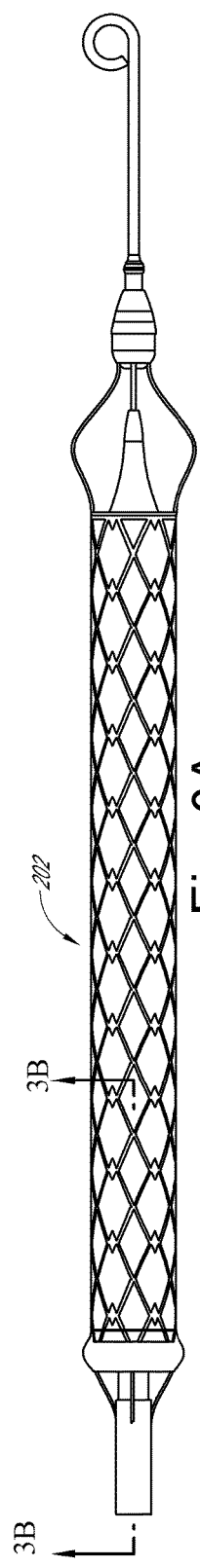
FIGS. 3A-3C illustrate the relative position of an impeller blade and an inner surface of an impeller housing in an undeflected configuration.
Figure 3B:
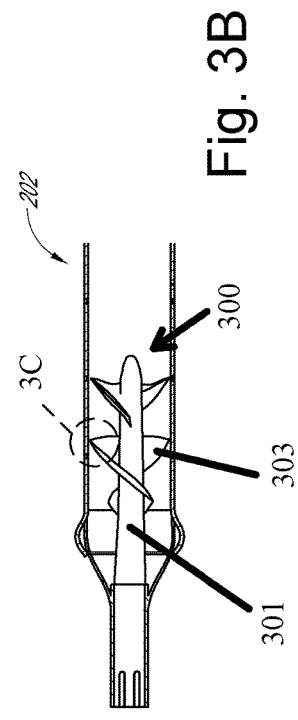
Figure 3C:
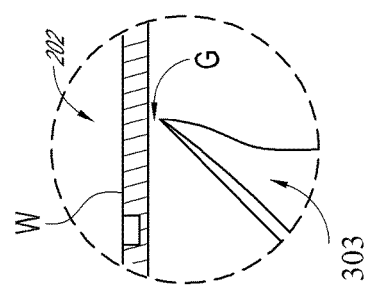
Figure 4:
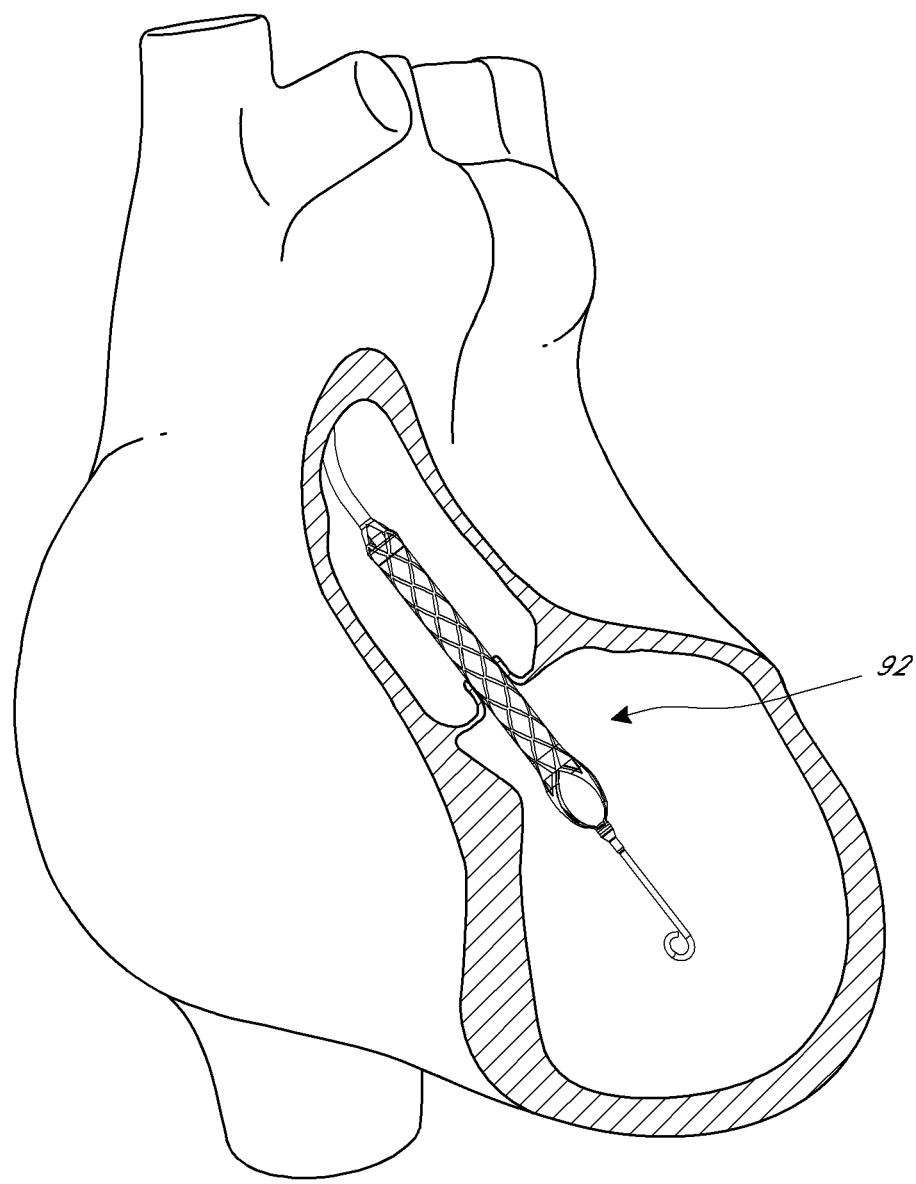
FIG. 4 shows the catheter assembly similar to that of FIG. 2 in position within the anatomy.

With reference to FIGS. 3A-3C, the operative device of the pump can include an impeller 300 having one or more blades 303. The one or more blades 303 can extend from an impeller hub 301. It can be desirable to increase the flow rate of the heart pump while ensuring that the impeller 300 can be effectively deployed within a subject. For example, an impeller can include one or more blades 303 that are configured to be inserted into a subject in a stored, or compressed, configuration. When the impeller 300 is positioned in the desired location, e.g., a chamber of a subject's heart as shown in FIG. 4, the blade(s) 303 of the impeller 300 can self-expand into a deployed or expanded configuration, in which the blade(s) 303 extends radially from a hub 301.

As shown in FIGS. 3A-3B, the impeller 300 can be positioned within a cannula or housing 202. A free end of the blades 303 can be separated from the wall W of the housing 202 by a tip gap G. The housing 202 can also have a stored, or compressed configuration, and a deployed or expanded configuration. The housing 202 and impeller 300 may deploy from the stored configurations from within the sheath assembly 88 into the expanded configuration. In such implementations, the sheath assembly 88 can keep the blade(s) 303 and the housing 202 compressed until the blade(s) 303 and housing 202 are urged from within a lumen of the sheath assembly 88. Once the blade(s) 303 are released from the sheath assembly, the blade(s) 303 can self-expand to a deployed configuration using strain energy stored in the blades 303 due to deformation of the blade(s) 303 within the sheath assembly 88. The expandable housing 202 may also self-deploy using stored strain energy after being urged from the sheath.

In the stored configuration, the impeller 300 and housing 202 have a diameter that is preferably small enough to be inserted percutaneously into a patient's vascular system. Thus, it can be advantageous to fold the impeller 300 and housing 202 into a small enough stored configuration such that the housing 202 and impeller 300 can fit within the patient's veins or arteries. In some embodiments, therefore, the impeller 300 can have a diameter in the stored configuration corresponding to a catheter size between about 8 Fr and about 21 Fr. In one implementation, the impeller 300 can have a diameter in the stored state corresponding to a catheter size of about 9 Fr. In other embodiments, the impeller 300 can have a diameter in the stored configuration between about 12 Fr and about 21 Fr. For example, in one embodiment, the impeller 300 can have a diameter in the stored configuration corresponding to a catheter size of about 12-12.5 Fr.

When the impeller 300 is positioned within a chamber of the heart, however, it can be advantageous to expand the impeller 300 to have a diameter as large as possible in the expanded or deployed configuration. In general, increased diameter of the impeller 300 can advantageously increase flow rate through the pump. In some implementations, the impeller 300 can have a diameter corresponding to a catheter size greater than about 12 Fr in the deployed configuration. In other embodiments, the impeller 300 can have a diameter corresponding to a catheter size greater than about 21 Fr in the deployed or expanded configuration.

In various embodiments, it can be important to increase the flow rate of the heart pump while ensuring that the operation of the pump does not harm the subject. For example, increased flow rate of the heart pump can advantageously yield better outcomes for a patient by improving the circulation of blood within the patient. Furthermore, the pump should avoid damaging the subject. For example, if the pump induces excessive shear stresses on the blood and fluid flowing through the pump (e.g., flowing through the cannula), then the impeller can cause damage to blood cells, e.g., hemolysis. If the impeller damages a large number of blood cells, then hemolysis can lead to negative outcomes for the subject. As will be explained below, various cannula and/or impeller parameters can affect the pump's flow rate as well as conditions within the subject's body.

When activated, the pump 10 can effectively increase the flow of blood out of the heart and through the patient's vascular system. In various embodiments disclosed herein, the pump 10 can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

C. Exemplary Left Ventricle Support Application

FIG. 4 illustrates one use of the catheter pump 10. A distal portion of the pump 10, which can include an impeller assembly 92, is placed in the left ventricle (LV) of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. No. 6,544,216; U.S. Pat. No. 7,070,555; and US 2012-

0203056A1, all of which are hereby incorporated by reference herein in their entirety for all purposes.

II. Structures for Supporting a Distal Bearing

When the operative device, including at least the expandable cannula and the impeller, are positioned within the patient, the operative device can be subject to bending loads. If the operative device is disposed in a heart chamber, the bending loads can be caused by movement of the beating heart or other external loads. The gap G between the blade(s) of the impeller and the internal wall of the expandable cannula can be very small, on the order of ten-thousandths of an inch. Due to the small gap between the cannula and the impeller blades, the bending loads can cause the impeller to contact the inner wall of the expandable cannula. When the impeller contacts the cannula while it rotates at high speed, the impeller and/or the cannula can be damaged. In addition, blood cell damage can result from contact between the impeller impacting the wall of the expandable cannula if, for example, the cells are caught between these components. Because the impeller rotates at high speed, an undesirable closing of the gap between the blade and cannula inner diameter for even a short time can lead to damage of a significant number of blood cells. Preventing damage to a large number of blood cells is advantageous, making the system less invasive by minimizing negative side effects of the use of the catheter pump system. Thus, while the small "tip gap" can advantageously improve the performance of the pump, the pump systems disclosed herein are advantageously configured to minimize the risk of adverse events (e.g. hemolysis and bleeding), which is generally undesirable in heart pump systems.

A. Exemplary Distal Bearing Support Having Improved Bending Stiffness

One approach to controlling tip gap is to improve the bending stiffness of the operative device. For example, the impeller and/or cannula housing can be configured to reduce movement of the impeller blade(s) relative to the inner wall of the cannula housing. In particular, increased stiffness of the operative device can reduce deflection of the impeller toward the cannula housing and/or deflection of the cannula housing toward the impeller. In one approach, the pump system is configured so that the impeller does not move significantly relative to the cannula housing, even though both can move together within the ventricle. In various embodiments, a distal bearing support can be disposed near, e.g., mounted, adjacent to a distal portion of the impeller shaft.

Figure 5A:
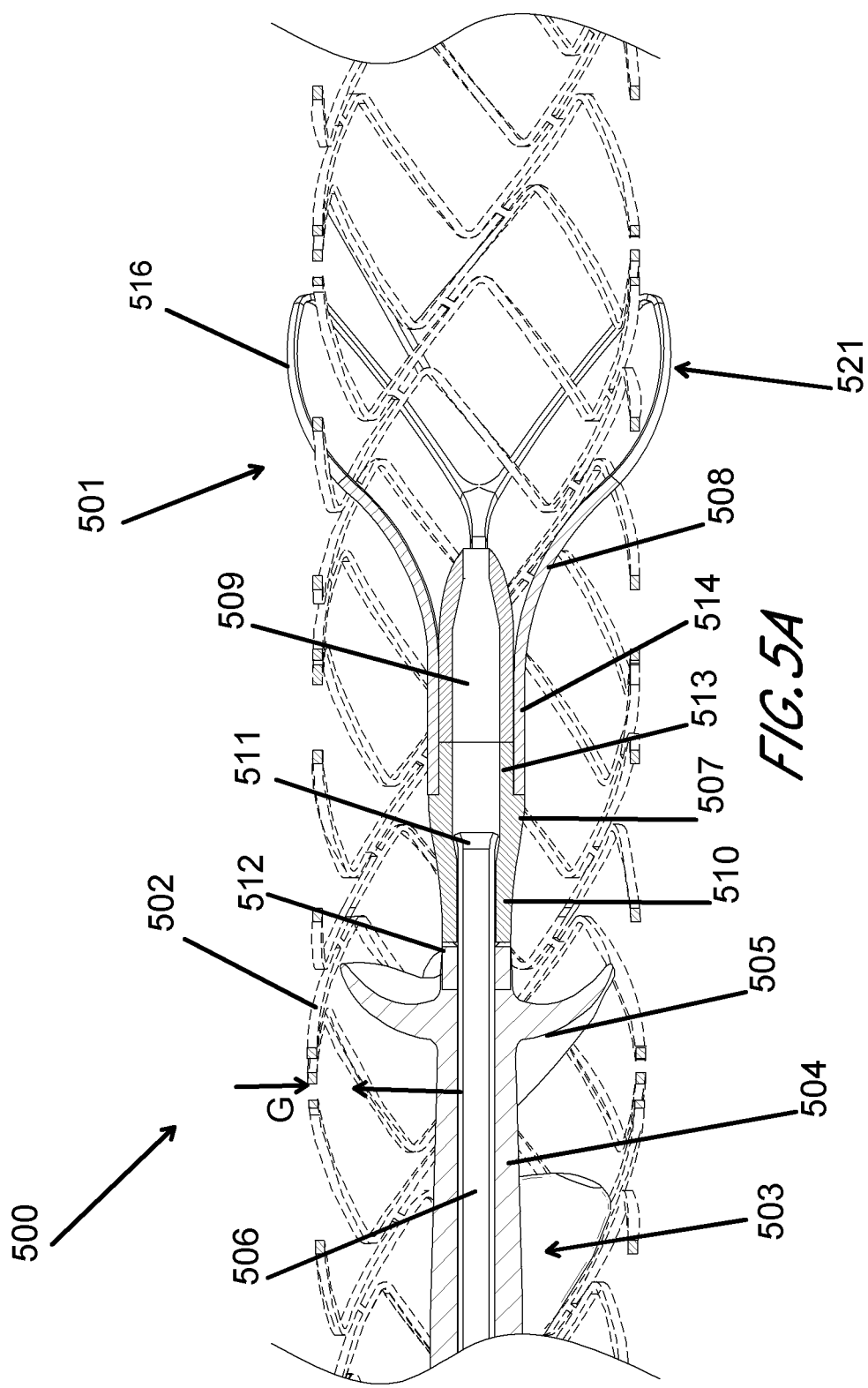

FIG. 5A is a side cross-sectional view of an operative device 500 of a catheter pump, according to one embodiment, having a support member in an expanded or relaxed configuration. FIG. 5B is a side cross-sectional view of the operative device 500 of FIG. 5A, with the support member illustrated as deployed within a cannula. For example, the operative device 500 can include a cannula housing 502, an impeller 503 disposed within the cannula housing 502, and one example of a distal bearing support 501 configured to improve the bending stiffness of the operative device 500. In FIG. 5A, the cannula housing 502 in an expanded configuration is shown in outline to compare a diameter of the expanded cannula housing 502 with a diameter of the distal bearing support 501 in a relaxed state. Thus, it should be appreciated that the configuration of FIG. 5A (e.g., showing the distal bearing support 501 as extending through the walls of the cannula housing 502) is for illustration purposes only.

The impeller 503 can include an impeller hub 504 and one or more blades 505 extending from the hub 504. The hub 504 can be mounted to an impeller shaft 506 such that the hub 504 is rotatably fixed relative to the impeller shaft 506, e.g., the hub 504 rotates with the shaft 506. As explained herein, the space between the free end of the blade(s) 505 and an inner wall of the cannula housing 502 can define a tip gap G. When the operative device 500 is subjected to bending loads, the free end of the blade(s) 505 may contact the inner wall of the cannula housing 502. As explained above, blood flowing between the free end of the blade(s) 505 and the cannula housing 502 may be damaged when the blade(s) 505 impacts the cannula housing 505, which can negatively affect patient outcomes.

As shown in FIG. 5A, the distal bearing support 501 can comprise a mounting portion 507 coupled to a distal portion of the impeller shaft 506, a support member 508 coupled to the mounting portion 507, and a nose member 509 (also referred to as a cap in some arrangements) disposed distal of the mounting portion 507. The nose member 509 can be disposed within and can be coupled to the support member 508. Preferably, the mounting portion 507, nose member 509, and support member 508 are configured to be non-rotatably mounted to the impeller shaft 506. For example, at least a proximal portion 510 of the mounting portion 507 disposed over a distal portion 511 of the impeller shaft 506 can have an inner diameter that is greater than an outer diameter of the impeller shaft. The impeller shaft 506 can therefore rotate relative to the mounting portion 507, such that the mounting portion 507 does not rotate with the impeller shaft 506. The interface between the mounting portion 507 and the impeller shaft 506 is preferably relatively low friction to minimize heat generation and a torque resistance applied to the distal end 511 of the impeller shaft 506.

During assembly of the distal bearing support 501, the mounting portion 507 can slide over the distal end 511 of the impeller shaft 506. As discussed above, the mounting portion 507 may be journaled in, e.g., not rotationally fixed relative to, the impeller shaft 506 in the illustrated embodiment. In some embodiments, a tool can be inserted into the distal end 511 of the impeller shaft 506 to flare the distal end 511 to make it wider than the proximal portion 510 of the mounting portion 507, e.g., the portions of the mounting portion 507 situated around the impeller shaft 506 proximal to the flared distal end 511. The flared distal end 511 can thereby prevent mounting portion 507 from translating distally and disengaging from the impeller shaft 506. In some embodiments, the mounting portion 507 can be made of a polymer, such as PEEK. Because the mounting portion 507 is not fixed relative to the impeller shaft 506, the impeller shaft 506 is free to rotate within the mounting portion 507. Moreover, in some aspects, an optional ring member 512 can be positioned around the impeller shaft 506 between the mounting portion 507 and the impeller 503. The ring member 512 can act as an interface between the impeller 503 and the mounting portion 507, and in some implementations, can be formed of a Teflon® (PTFE) or other low friction material.

As shown in FIGS. 5A-5B, the support member 508 can be disposed over a distal portion 513 of the mounting portion 507. The distal portion 513 of the mounting portion 507 can include a necked or stepped region to engage the support member 508. A mechanical connection may be provided between the support member 508 and another rotationally fixed portion of the distal bearing support 501, e.g., between a proximal portion of the support member 508 and the mounting portion 507. For example, the mounting portion 507 can include one or more barbs (not shown) positioned around the circumference of the mounting portion 507. In some implementations, the barbs are located every 120 degrees about the circumference. The barbs can engage corresponding slots in the support member 508 to secure the support member 508 to the mounting portion 507. The barbs could alternatively be formed on the support member 508 and configured to extend into and engage the mounting portion 507 in one embodiment. In some arrangements, an adhesive connection is provided between the mounting portion 507 and support member 508 in place of or in addition to the mechanical connection. In another embodiment, the support member 508 and mounting portion 507 are portions of a unitary body, which can be formed from a cylindrical precursor tube. In some embodiments, the support member can be formed of nitinol.

The nose member 509 can be positioned distal of the mounting portion 507 and within the proximal portion 514 of the support member 508. Like the mounting portion 507, the nose member 509 can additionally or alternatively include barbs (not shown) around the circumference of the nose member 509 (e.g., separated by 120 degrees) to engage corresponding slots in the support member 508. The nose member 509 can be configured to smooth out the flow of blood through the cannula housing 502 in the zone of the distal bearing support 501, e.g., distal of the impeller 503.

Thus, the mounting portion 507 can be mounted about the impeller shaft 506 (restrained axially by the flared portion 511 but otherwise rotationally decoupled from the impeller shaft 506), the support member 508 can couple to the mounting portion 507 via the barbs, and the nose member 509 can couple to the support member 508 via additional barbs. In some embodiments a single continuous member is provided that combines the function of the nose portion 509 and mounting portion 507. For example, these components can be formed as a unitary component to which the support member may be coupled.

The support member 508 can include a stiffener structure, e.g., a skeleton, cage-like, or other flexible structure that extends distally from or of the nose member 509 and/or mounting portion 507. For example, the support member 508 may include one or more lobes 516 or digits biased to expand radially outward. As shown in FIG. 5A, the support member 508 can be sized and shaped such that the radial distance from one or more of the lobes 516 or digits to a projection of the longitudinal axis of the impeller shaft 506 in their natural, relaxed state is greater than the radial distance from the cannula wall to a projection of the longitudinal axis of the impeller shaft 506 when the cannula 502 is in an operational (e.g., expanded) configuration. When the lobes 516 or digits are positioned within the cannula 502 with the cannula 502 in an expanded state (e.g., as in FIG. 5B), the digits or lobes 516 can apply a radially outward force against the inner wall of the cannula housing 502. This radially outward force can increase the bending stiffness of the cannula housing 502. By increasing the bending stiffness of the cannula housing 502, the disclosed distal bearing support 501 can reduce the risk of hemolysis during operation of the pump.

As shown in FIGS. 5A-5B, the lobes 516 may comprise an elongate member, e.g., an elongate arcuate member or compound curve, extending from the proximal portion 514 of the support member 508. The lobes 516 can include a concave portion 522 disposed between the proximal portion 514 of the support member 508 and a free end of the lobes, e.g., near the proximal portion 514 in some arrangements. The concave portion 522 can be curved inwardly towards the interior of the cannula 502. Furthermore, the lobes 516 can have a convex portion 521 in contact with a support region 520 of the cannula housing 502. The convex portion 521 can be curved outwardly towards the wall of the cannula 502 in some embodiments. It should be appreciated that, due to the radially outward bias of the lobes 516, the convex portion 521 of the lobes 516 may induce a radially outward force against the cannula housing 502 at the support region 520, where the convex portion 521 contacts the cannula housing 502.

Various embodiments of the cannula housing 502 may comprise a mesh of metallic material that is coated by an elastic film. In some cases, the radially outward force applied by the convex portions 521 against the cannula housing 502 may deform or otherwise damage the metallic mesh and/or the elastic covering film. To prevent deformation of the cannula housing 502 and/or damage to the elastic film, in some embodiments, the metallic mesh may be made denser at the support region 520 of the cannula wall that contacts the convex portions 521 than in other locations of the cannula housing 502. The additional metallic material at the support region 520 near the convex portions 521 can provide additional support for the housing 502 and elastic film to prevent undesirable deformation of the housing 502 and/or film.

In the illustrated embodiment, the support member 508 deploys into a flower-shape, e.g., the lobes 516 may form the shape of flower petals, and/or non-planar, compound curve or isomorphic shape. The exemplary embodiment has four lobes 516. Each lobe 516 may be formed or defined by a pair of proximal struts 523 and a pair of distal struts 524. As shown in FIG. 5B, for example, each proximal strut 523 may be coupled or formed with the proximal portion 514 of the support member 508. The proximal struts 523 may be spaced apart circumferentially about the mounting portion 507 and/or the nose member 509. Distal ends of the proximal struts 523 may couple to proximal ends of the distal struts 524, as shown in FIGS. 5A-5B. Distal ends of the distal struts 524 may couple to one another. As shown in FIG. 5B, for example, the convex portion 521 of the lobes 516 may be disposed between the proximal and distal ends of the distal struts 524.

As shown in FIG. 5B, a distal end 515 of each of the exemplary lobes 516 may extend generally parallel with the cannula housing and curves slightly inward at its tip toward the impeller axis to avoid the edges from cutting into the cannula housing 502. Further, the outer curved faces of the lobes 516 or digits may not be rigidly fixed to the inner surface of the cannula housing 502 but, instead, relative movement between the two may be possible. This relative movement enables easier expansion and collapsing of the operative device of the catheter pump system. One will appreciate from the description herein that the support member 508 stored and deployed configurations can be modified depending on the application, and in various examples, based on the impeller and cannula housing designs.

B. Exemplary Distal Bearing Support With Enhanced Maneuverability

While the distal bearing support of FIGS. 5A-5B can advantageously stiffen the operative device of the catheter pump system, the support member extends distally beyond the distal end of the impeller shaft (and/or the impeller). Because the stiff support member extends beyond the distal end of the impeller and/or impeller shaft (e.g., axially displaced from the distal end of the impeller shaft), a length of the catheter pump extending from a proximal portion of the impeller to the distal end of the support member can have a relatively high bending stiffness, because this portion includes the relatively stiff impeller in addition to the support member. This length can be referred to as the "stiff length." A long stiff length can be disadvantageous because it can hamper maneuverability when the catheter pump (the operative device) is urged through the arcuate-shaped aortic arch. Thus, it can be desirable to decrease the length of the "stiff length" portion of the catheter pump while still maintaining a high bending stiffness when the operative device is positioned in or near a heart chamber, e.g., the left ventricle.

1. Exemplary Distal Bearing Support for Enhanced Maneuverability of the Operative Device FIG. 6A is a side cross-sectional view of an operative device 600 of a catheter pump, according to another embodiment, with a support member in an expanded or relaxed configuration. FIG. 6B is a side cross-sectional view of the operative device 600 of FIG. 6A, with the support member illustrated as being disposed in a cannula. Unless otherwise noted, the reference numerals of FIGS. 6A-6B may refer to components similar to those referenced above in FIGS. 5A-5B, incremented by 100 relative to FIGS. 5A-5B. For example, the operative device 600 can include a cannula housing 602, an impeller 603 disposed within the cannula housing 602, and another example of a distal bearing support 601 configured to improve the bending stiffness and maneuverability of the operative device 600. The impeller 603 can include an impeller hub 604 mounted on an impeller shaft 606 and one or more blades 605 extending from the hub 604. As with FIG. 5A above, FIG. 6A illustrates the distal bearing support 601 in a relaxed state for illustration purposes only.

As in FIGS. 5A-5B, the distal bearing support 601 can include a nose member 609 or cap configured to smooth the flow of blood. In addition, the distal bearing support 601 can include a support member 608 having a plurality of lobes 616 extending radially outward with a radially outward bias when positioned in the cannula housing 602. As in FIGS. 5A-5B, the lobes 616 can include a concave portion 622 and a convex portion 621 that contacts the mesh of the cannula housing 602 at a support region 620. Further, the lobes 616 can include an arcuate member with a pair of separate proximal struts 623, and a pair of distal struts 624 coupling at their distal ends.

However, unlike the distal bearing support 501 in FIGS. 5A-5B, the distal bearing support 601 of FIGS. 6A-6B can provide a reduced stiff length, while increasing the bending stiffness when the pump is positioned within a heart chamber. As illustrated in FIGS. 6A-6B, at least a proximal portion 614 of the support member 608 axially overlaps with the impeller shaft 606, as opposed to being axially displaced from the distal end 511 of the impeller shaft 506, as in the embodiment of FIG. 5A. Stated another way, an axial gap or spacing is provided between the distal-most aspect of the impeller shaft 506 (e.g., the distal end 511) and the proximal-most aspect of the support member 508 in the embodiment of FIG. 5A, whereas no axial gap is provided between the distal-most aspect 611 of the impeller shaft 606 and the proximal-most aspect of the support member 608 in the embodiment of FIG. 6A. The length of the stiff portions (e.g. the "stiff length") can thereby be reduced as compared with the embodiment of FIGS. 5A-5B. Indeed, because the support member 608 of FIGS. 6A-6B extends distally beyond the distal end 611 of the impeller shaft 606 by a lesser amount than the support member 508 of FIGS. 5A-5B, the stiffness of the operative device 600 may be less in the embodiment of FIGS. 6A-6B. The operative device 600 of FIG. 6 may therefore be easily maneuvered over the aortic arch during insertion.

For example, in FIG. 6A, a mounting portion 607 (e.g., an interface material) can be positioned over, e.g., formed around, the impeller shaft 606 to rigidly couple to the shaft 606. In some embodiments, the mounting portion 607 can comprise a PEEK heat shrink material that can be applied over the impeller shaft 606 and can rotate with the shaft 606. For instance, the heat shrink material can be applied before forming the impeller 603, e.g., by casting. The nose member 609 can be molded to the impeller shaft 606. In some embodiments, the distal end 611 of the impeller shaft 606 can include engagement features 632 for enhancing security of the nose member 609 to the shaft 606. The engagement features 632 can include circumferential recesses or holes, e.g., formed by laser drilling. When the nose member 609 is molded over the distal end 611, portions of the nose member 609 can reflow into the circumferential holes to help secure the nose member 609 to the distal end 611 of the impeller shaft 606.

The proximal portion 614 of the support member 608 can be mounted over the mounting portion 607 to secure the support member 608 to the impeller 603. In some embodiments, a nitinol support member 608 can be cooled to expand the proximal end 614 of the support member 608 to allow the proximal end 614 to be urged over the mounting portion 607. When the support member 608 returns to room temperature, the nitinol can return to its original size. The proximal end 614 of the support member 608 can include one or more slots circumferentially spaced from one another on the proximal end 614 of the support member 608. Each of the one or more slots can extend from the proximal-most side of the support member 608 distally and terminate at a wider hole region. The slots can be formed through the thickness of the proximal end portion 614 of the support member 608. In some embodiments, the slots extend through the entire thickness of the proximal end portion 614 of the support member 608, but in other embodiments, the slots may only extend partially through the thickness. The slots can be used to expand or flare out the proximal end 614 of the support member 608 when the support member 608 is urged over the nose member 609 to couple to the mounting portion 607. This expansion or flaring can advantageously assist in mounting the support member 608 over the nose member 609. The mounting portion 607 (spinning with the impeller shaft 606) can freely rotate within the proximal end 614 of the support member 608. As above, the support member 608 can provide enhanced bending stiffness. In addition, as explained herein, the support member 608 can provide improved maneuverability of the operative device 600 by reducing the stiff length of the operative device 600.

2. Exemplary Maneuverable Distal Support With Sealable Guide Wire Lumen

Although the distal bearing support 601 illustrated in FIGS. 6A-6B can provide improved bending stiffness and a reduced stiff length, there may be a few potential problems with the embodiment of FIGS. 6A-6B. For example, the molded nose member 609 of FIGS. 6A-6B may be susceptible to damage during operation of the pump, and the nose member 609 may break off the impeller shaft 606 under various operational or environmental conditions. Moreover, in the embodiment of FIGS. 6A-6B, the support member 608 can translate axially in the distal direction, which may cause the support member 608 to jam against the nose member 609 when the support member 608 translates distally. If the support member 608 bears against the nose member 609, the nose member 609 could break, or the resulting distally-directed force could slow or stop rotation of the impeller shaft 606.

Furthermore, when a Seldinger insertion technique is used to advance the operative device to the heart, a guidewire and guidewire guide tube may be used. For example, the guidewire guide tube may be disposed through a central lumen of the catheter pump. The clinician can insert a guidewire through the guidewire guide tube, and can advance the guidewire to the heart. After advancing the operative device over the guidewire and into the heart, the guidewire and guidewire guide can be removed from the catheter pump. When the guidewire guide tube and/or the guidewire is retracted through a distal portion of the nose member 609, the distal portion may not adequately reseal the lumen through the impeller shaft. Accordingly, there is a need for an improved distal bearing support that provides for a re-sealable nose member and an improved support member.

Figure 7A:
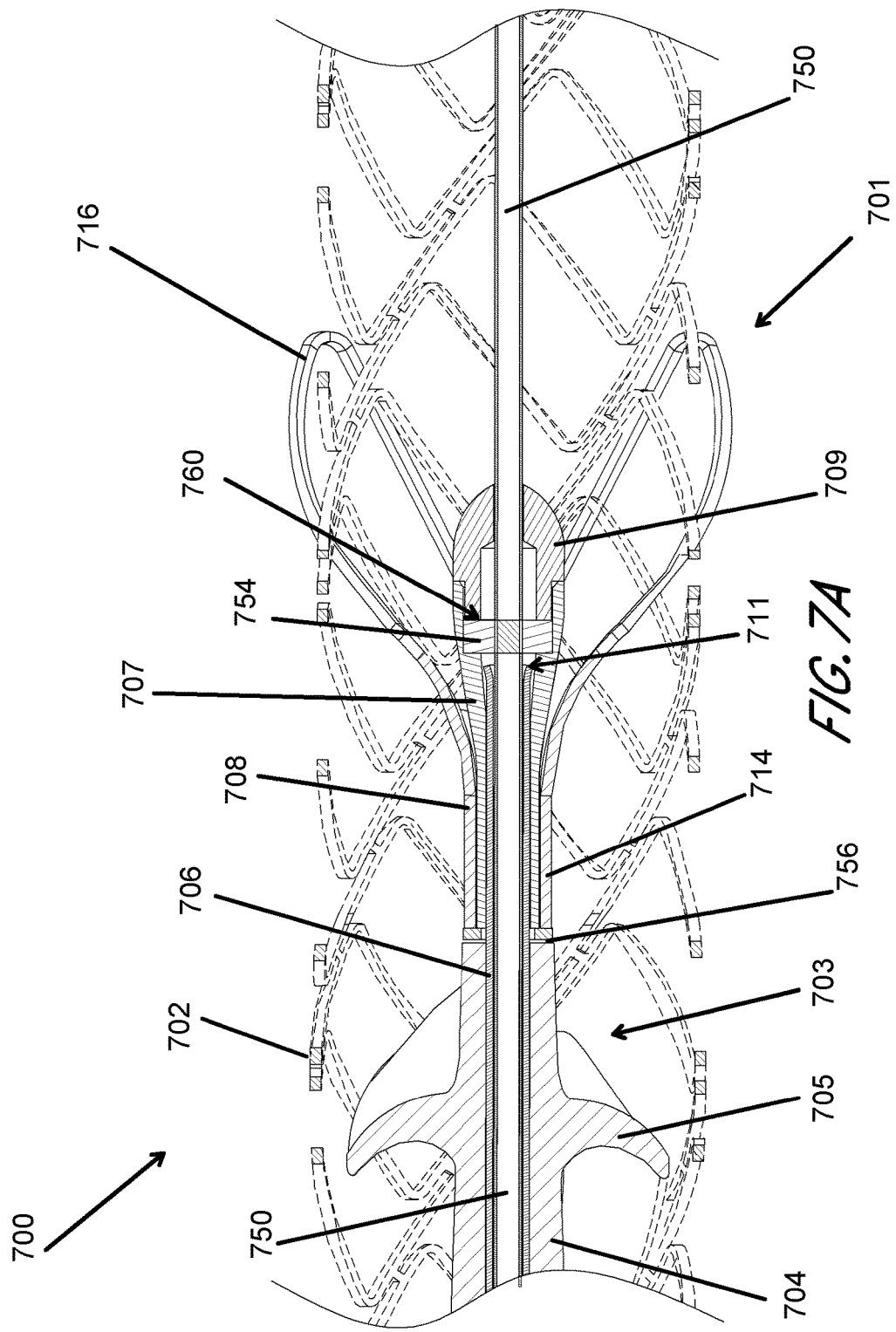
FIGS. 7A and 7B show cross-sectional views of yet another embodiment of a distal bearing support, and also illustrate a guide wire guide device.
Figure 7B:
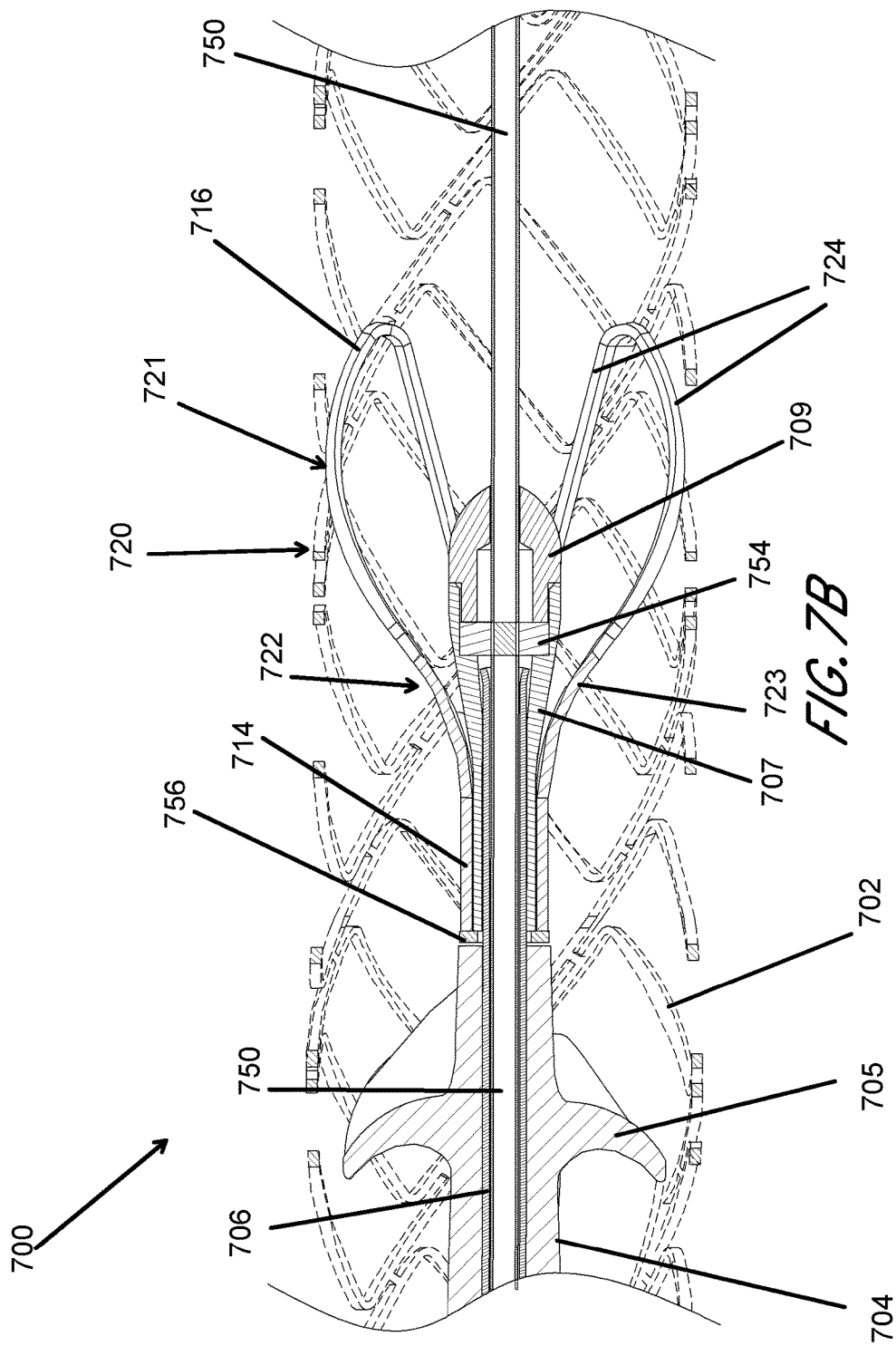

FIG. 7A is a side cross-sectional view of an operative device 700 of a catheter pump, according to another embodiment, with a support member in an expanded or relaxed state or configuration. FIG. 7B is a side cross-sectional view of the operative device 700 of FIG. 7A, with the support member shown as being disposed in the cannula. Unless otherwise noted, the reference numerals of FIGS. 7A-7B may refer to components similar to those referenced above in FIGS. 5A-5B and 6A-6B, incremented by 100 relative to FIGS. 6A-6B. For example, the operative device 700 can include a cannula housing 702, an impeller 703 disposed within the cannula housing 702, and another example of a distal bearing support 701 configured to improve the bending stiffness and maneuverability of the operative device 700. The impeller 703 can include an impeller hub 704 mounted on an impeller shaft 706 and one or more blades 705 extending from the hub 704. As with FIG. 5A above, FIG. 7A illustrates the distal bearing support 701 in a relaxed state for illustration purposes only.

In addition, as in FIGS. 5A-5B and 6A-6B, the distal bearing support 701 can include a nose member 709 or cap configured to smooth the flow of blood. The distal bearing support 701 can also include a mounting portion 707 configured to mount to the impeller shaft 706, and a support member 708 coupled to the mounting portion. The support member 708 can have a plurality of lobes 716 extending radially outward with a radially outward bias when positioned in the cannula housing 702. The lobes 716 can include a concave portion 722 and a convex portion 721 that contacts the mesh of the cannula housing 702 at a support region 720. Further, the lobes 716 can include an arcuate member with a pair of separate proximal struts 723, and a pair of distal struts 724 coupling at their distal ends. In addition, a guidewire guide tube 750 can pass through the impeller shaft 706. As explained above, a guidewire can be advanced through the guidewire guide tube and into the patient's anatomy. As with FIGS. 6A-6B, a proximal portion 714 of the support member 708 overlaps a distal end 711 of the impeller shaft, which can reduce the stiff length of the operative device 700.

The support member 708 can initially be mounted loosely over the distal portion 711 of the impeller shaft 706. A spacer or washer 756 (e.g., formed of nitinol) can be formed at or near the proximal end portion 714 of the support member 708 to prevent distal motion of the support member 708 in the axial direction. For example, the washer 756 can be welded to the proximal end 714 of the support member 708 in some embodiments. The mounting portion 707 can be glued or otherwise secured to the impeller shaft 706 within the support member 708 such that the mounting portion 707 rotates with the shaft 706 in some embodiments. In other embodiments, the impeller shaft 706 may be free to rotate relative to the mounting portion 707. An optional flare portion at the distal end 711 of the impeller shaft 706 can be formed (like in FIG. 5A) to prevent the mounting portion 707 from translating in the distal direction relative to the shaft 706. The distal end 711 of the impeller shaft, which can include the flared portion, may be disposed in a recess of an enlarged distal portion of the mounting portion 707 (e.g., an interface member). As shown, a proximal portion of the mounting portion 707 can include a bushing portion disposed about the impeller shaft 706 near the proximal portion 714 of the support member 708. The flared portion of the distal end 711 of the impeller shaft 706 can have a diameter larger than the bushing portion.

A re-sealable member 754, or a septum, can be inserted within a stepped region or recess near the distal end 760 of mounting portion 707, e.g., into an enlarged portion disposed distal the enlarged portion in which the distal end 711 of the impeller shaft 706 is disposed. The re-sealable member 754 can be employed to reseal the aperture formed when the guidewire and/or guidewire guide 750 (e.g., made of stainless steel) is removed. For example, the mounting portion 707 can press against the re-sealable member 754 to compress or force the re-sealable member 754 radially inward, such that the re-sealable member 754 is pre-loaded to re-seal the lumen when the guidewire guide 750 and/or guidewire is removed. In some embodiments, the re-sealable member 754 may not rotate relative to the impeller shaft 706 and/or the mounting portion 707. In other embodiments, the re-sealable member 754 may rotate with the mounting portion 707. The re-sealable member 754 can be a self-healing polymer and/or a high durometer polymer, or any other polymer suitable for resealing the guidewire guide 750. As shown in FIGS. 7A-7B, the re-sealable member 754 can be disposed distally of the impeller shaft 706 in the stepped region or recess of a distal portion of the mounting portion 707 (e.g., an interface member). In addition, the flared portion at the distal end 711 can be disposed in or near the recess that includes the re-sealable member 754.

The nose member 709 can be installed within the distal end 760 of the mounting portion 707. Barbs within the nose member 709 can engage with slots located in the mounting portion 707. Because the nose member 709 couples to the mounting portion 707, and because the mounting portion 707 couples to the impeller shaft 706, both the nose member 709 and the mounting portion 707 can rotate with the impeller 703. The support member 708 can remain rotationally fixed, such that the support member 708 does not rotate with the impeller 703.

In the implementation of FIGS. 7A-7B, therefore, the stiff length may be reduced while also introducing a resealing member (a "septum") to prevent fluid from entering the apertures formed when the guidewire guide tube is retracted after using a guidewire with the Seldinger technique. In addition, the washer 756, which may be coupled to the proximal end of the support member 708, prevents distal axial translation of the support member 708. By securing the support member 708 in the distal direction, the distal bearing support 701 can advantageously avoid damaging the nose member 709 and/or jamming the impeller 703 due to translation of the support member 708.

Modifications of catheter pumps incorporating a catheter assembly with a distal impeller support can be used for right side support. For example, a catheter body carrying the impeller and distal bearing support can be formed to have a deployed shape corresponding to the shape of the vasculature traversed between a peripheral vascular access point and the right ventricle. One will appreciate from the description herein that the catheter assembly may be modified based on the respective anatomy to suit the desired vascular approach. For example, the catheter assembly in the insertion state may be shaped for introduction through the subclavian artery to the heart. The catheter pump may be configured for insertion through a smaller opening and with a lower average flow rate for right side support. In various embodiments, the catheter assembly is scaled up for a higher flow rate for sicker patients and/or larger patients.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. An apparatus for inducing motion of a fluid relative to the apparatus, comprising:
   a motor;
   an elongated catheter body coupled with the motor and comprising a distal portion;
   an expandable cannula disposed at the distal portion and comprising an inlet and an outlet, the expandable cannula having a delivery profile and an operational profile larger than the delivery profile;
   an impeller mounted on an impeller shaft connected to the motor, the impeller disposed within the expandable cannula between the inlet and the outlet, the impeller comprising at least one impeller blade;
   an expandable distal bearing support coupled to and extending distally from the impeller shaft within the expandable cannula, the expandable distal bearing support having an arcuate outer surface in contact with an internal wall of the expandable cannula at least when the expandable cannula is in the operational profile, and configured to provide radial support of the impeller shaft within the expandable cannula;
   wherein operation of the motor causes rotation of the impeller to draw blood into the lumen.

2. The apparatus of claim 1, wherein the motor is disposed at a proximal end of the elongate catheter body, wherein the motor is configured to remain remote from the impeller and to remain outside a patient.

3. The apparatus of claim 1, further comprising a re-sealable member disposed distally of the impeller within the expandable distal bearing support.

4. The apparatus of claim 3, wherein the re-sealable member is coupled to the impeller shaft to enable the impeller shaft to rotate in the expandable distal bearing support, wherein the re-sealable member is held stationary with respect to the impeller shaft and distal of but aligned with the impeller.

5. The apparatus of claim 1, wherein the expandable distal bearing support comprises an elongate member having a convex portion in contact with an internal wall of the expandable cannula.

6. The apparatus of claim 5, wherein the expandable cannula comprises a mesh.

7. The apparatus of claim 6, wherein the mesh is denser at a support region of the expandable cannula that contacts the convex portion than in another region of the expandable cannula.

8. The catheter pump of claim 5, wherein the elongate member comprises a proximal end coupled with a mounting portion of the expandable distal bearing support, a free distal end, and a concave portion disposed between the proximal end and the free distal end.

9. The catheter pump of claim 5, wherein the expandable distal bearing support comprises first and second proximal struts spaced circumferentially from each other and first and second distal struts coupled to each other at distal ends thereof, the proximal ends of the distal struts being coupled with distal ends of the proximal struts.

10. The catheter pump of claim 9, wherein the convex portion is disposed between the proximal and distal ends of the distal struts.

11. The catheter pump of claim 1, wherein the expandable distal bearing support comprises a mounting portion having a cylindrical member disposed on the impeller shaft in a manner permitting the impeller shaft to rotate therein.

12. The catheter pump of claim 11, wherein the impeller shaft has an enlarged diameter at a distal end thereof and the cylindrical member has a diameter less than the enlarged diameter at the proximal end thereof.

13. The catheter pump of claim 12, wherein the cylindrical member comprises an enlarged distal portion having an inner diameter greater than the enlarged diameter at the distal end of the impeller shaft.

14. The catheter pump of claim 13, further comprising a re-sealable septum disposed in the enlarged distal portion of the cylindrical member.

15. The catheter pump of claim 13, further comprising a cap coupled with the distal end of the cylindrical member, the cap having a rounded distal portion with an aperture for passage of a guidewire through the impeller.

16. The catheter pump of claim 1, further comprising a spacer disposed between the impeller and a proximal end of the expandable distal bearing support.

17. The catheter pump of claim 1, wherein the impeller is expandable.

18. An apparatus for inducing motion of a fluid relative to the apparatus, comprising:
   a motor;
   an elongated catheter body coupled with the motor, the elongated catheter body including a distal portion;
   an expandable cannula disposed at the distal portion about a lumen and having an inlet and an outlet;
   an impeller mounted on an impeller shaft connected to the motor, the impeller disposed within the expandable cannula and comprising at least one impeller blade;
   a distal bearing support having an arcuate outer surface in contact with an internal wall of the expandable cannula during at least a portion of a treatment procedure, the distal bearing support coupled to and extending distally from the impeller shaft within the expandable cannula and configured to provide radial support of the impeller shaft within the expandable cannula;
   wherein operation of the motor causes rotation of the impeller to draw blood into the lumen.

19. The apparatus of claim 18, wherein the distal bearing support is expandable.

20. The apparatus of claim 18, wherein the distal bearing support comprises an elongate member having a convex portion in contact with an internal wall of the expandable cannula.

21. The apparatus of claim 18, wherein the motor is sized and shaped so as to be insertable into a body of a patient.

\* \* \* \* \*